United States Patent
McNeil-Watson

(10) Patent No.: US 9,341,564 B2
(45) Date of Patent: May 17, 2016

(54) APPARATUS FOR HIGH-THROUGHPUT SUSPENSION MEASUREMENTS

(75) Inventor: Fraser McNeil-Watson, Malvern (GB)

(73) Assignee: Malvern Instruments, Ltd., Malvern, Worcestershire (GB)

(*) Notice: Subject to any disclaimer, the term of this patent is extended or adjusted under 35 U.S.C. 154(b) by 1089 days.

(21) Appl. No.: 13/123,518

(22) PCT Filed: Oct. 9, 2009

(86) PCT No.: PCT/GB2009/051350
§ 371 (c)(1), (2), (4) Date: Dec. 7, 2011

(87) PCT Pub. No.: WO2010/041082
PCT Pub. Date: Apr. 15, 2010

(65) Prior Publication Data
US 2012/0073972 A1    Mar. 29, 2012

Related U.S. Application Data

(60) Provisional application No. 61/195,647, filed on Oct. 9, 2008, provisional application No. 61/206,688, filed on Feb. 3, 2009.

(51) Int. Cl.
*G01N 27/453* (2006.01)
*G01N 21/25* (2006.01)
(Continued)

(52) U.S. Cl.
CPC ............ *G01N 21/253* (2013.01); *B01L 3/5025* (2013.01); *G01N 21/51* (2013.01);
(Continued)

(58) Field of Classification Search
CPC ....... G01N 21/47; G01N 21/49; G01N 21/51; G01N 2021/4702; G01N 2021/513; G01N 27/44721
See application file for complete search history.

(56) References Cited

U.S. PATENT DOCUMENTS 4,046,667 A * 9/1977 Goetz ........................... 204/645
4,061,543 A * 12/1977 Bean et al. ...................... 435/32
(Continued)

FOREIGN PATENT DOCUMENTS

EP    1154266    11/2001
EP    1447454    8/2004
(Continued)

OTHER PUBLICATIONS

Oddy M.H. & J.G. Santiago; "A method for determning electrophoretic and electroosmotic mobilities using AC and DC electric field particle displacements"; Journal of Colloid and Interface Science; Sep. 23, 2003; pp. 192-204; vol. 269, No. 1.
(Continued)

*Primary Examiner* — Alexander Noguerola
(74) *Attorney, Agent, or Firm* — Kristofer E. Elbing

(57) ABSTRACT

A high-throughput optical suspension characterization instrument is disclosed, which can include hydraulically separate and at least partially transparent sample containers. A selection mechanism is operative to selectively direct light from a light source (12) through different ones of the sample containers along an optical axis, and an off-axis scattering detector (38,24) is responsive to scattered light from the light source after it has interacted with a sample. Phase analysis light scattering is used to determine the electrophoretic mobility and zeta potential of samples. A second instrument is disclosed, wherein all sample containers are illuminated simultaneously. Transmitted light is collected by a camera. The electrophoretic mobility and hydrodynamic size of the samples may be determined.

34 Claims, 5 Drawing Sheets

(51) Int. Cl.
*B01L 3/00* (2006.01)
*G01N 21/51* (2006.01)
*G01N 27/447* (2006.01)
*G01N 21/03* (2006.01)
*G01N 15/14* (2006.01)
*G01N 21/47* (2006.01)

(52) U.S. Cl.
CPC .. *B01L2300/0829* (2013.01); *B01L 2400/0421* (2013.01); *G01N 21/03* (2013.01); *G01N 27/44721* (2013.01); *G01N 2015/1493* (2013.01); *G01N 2021/0346* (2013.01); *G01N 2021/4707* (2013.01); *G01N 2021/513* (2013.01); *G01N 2201/103* (2013.01); *G01N 2201/105* (2013.01)

(56) References Cited

U.S. PATENT DOCUMENTS

| | | | |
|---|---|---|---|
| 4,101,220 A | | 7/1978 | Bean |
| 4,217,195 A | * | 8/1980 | Uzgiris et al. ............... 205/149 |
| 5,324,401 A | | 6/1994 | Yeung |
| 6,519,032 B1 | * | 2/2003 | Kuebler et al. ............... 356/337 |
| 2004/0248117 A1 | | 12/2004 | Kosak |
| 2006/0087522 A1 | * | 4/2006 | Muller-Hartmann et al. .... 347/1 |
| 2006/0114467 A1 | | 6/2006 | Nicoli |

FOREIGN PATENT DOCUMENTS

| | | |
|---|---|---|
| GB | 2399879 | 9/2004 |
| WO | 8802482 | 4/1988 |
| WO | 03071269 | 8/2003 |

OTHER PUBLICATIONS

Gong X & E.S. Yeung; "An Absorption Detection Approach for Multiplexed Capillary Electrophoresis Using a Linear Photodiode Array"; Analytical Chemistry; Sep. 25, 1999; pp. 4989-4996; vol. 71, No. 21.

Gao Q et al; "Simultaneous genetic typing from multiple short tandem repeat loci using a 96-capillary array electrophoresis system"; Electrophoresis; Jun. 1, 1999; pp. 1518-1526; vol. 20, No. 7; Wiley Interscience, DE.

Ansari RR & Ki Suh; "Dynamic light scattering particle size measurements in turbid media"; Coherence Domain Optical Methods in Biomedical Science and Clinical Applications II; Jan. 27, 1998; vol. 3251; SPIE.

PCT Search Report for International application No. PCT/GB2009/051350, mailed Jun. 28, 2010.

* cited by examiner

APPARATUS FOR HIGH-THROUGHPUT SUSPENSION MEASUREMENTS

This application claims priority to provisional application No. 61/195,647 filed Oct. 9, 2008 and to provisional application No. 61/206,688 filed Feb. 3, 2009. The subject matter of this application is also related to that of U.S. Pat. No. 7,217,350, entitled "High & Low Frequency Electrophoresis" (Mc-Neil-Watson and Connah). All of these applications are herein incorporated by reference.

BACKGROUND

Measurements of the zeta potential of a particle or molecule reflect the state of charge at the hydrodynamic plane where the particle diffuses in the bulk fluid of a suspension. This diffusion is a random process dependant on particle size; when an electric field is applied there is also a directed component in the field direction and this causes a velocity that is linearly dependant on the zeta potential for low fields which do not cause distortion of the fluid around the particle. Measurement of the so called electrophoretic mobility (EPM) can be used to determine the potential. Although absolute measurements are important and can be used to predict dispersion stability, in many important cases it is changes that arise from some treatment of the sample that are observed. Such a change can occur when, for example, a positively charged macromolecule such as a protein binds to the surface of a negatively charged particle so reducing the effective EPM. Observing this reduction in EPM enables the binding process to be quantified and related to the presence of specific ligands on the particle, or the particular ionic constitution of the suspending fluid, such as its pH value or background salt concentration. Current instruments make measurements of individual samples typically of a few hundred microliters of sample, and can measure automatically sequences of samples if they are provided from an autosampler or autotitrator. A typical instrument representing the current 'state of the art' is described in Appendix 1 of this document.

To rapidly assess many different samples, representing perhaps different binding proteins, or different concentrations of these, and different ligand particles, a faster method would be very useful.

SUMMARY

In one general aspect, the invention features a high-throughput optical suspension characterization instrument that includes a plurality of hydraulically separate and at least partially transparent sample containers. A selection mechanism is operative to selectively direct light from a light source through different ones of the sample containers along an optical axis, and an off-axis scattering detector is responsive to scattered light from the light source after it has interacted with a sample.

In preferred embodiments the selection mechanism can be operative to move the sample containers together relative to the light source and the detector. The selection mechanism can include a motorized X-Y stage. The selection mechanism can include a motorized X-Y-Z stage. The sample containers can be part of a unitary sample container array. The sample containers can be part of a 96-well plate. The light source can be a laser. The instrument can further include a top window associated with each of the sample containers that includes at least a portion located in an off-axis scattering path between a light source position and the scattering detector. Each window can be a partial window and can be integral to one of the sample containers. The instrument can further include a pair of electrodes associated with each of the sample containers. The electrodes can be integral to the containers. The electrodes can be part of a removable electrode assembly. The instrument can further include an electrical probe associated with a receiving lens and wherein the electrical probe is operative to selectively make an electrical connection to one of the electrodes for a selected one of the sample containers. The selection mechanism can include a motorized mechanism operative to position the probe vertically. The instrument can further include sequencing logic operative to cause the selection mechanism to successively select and perform a measurement for each of a plurality of the different sample containers. The instrument can further include an optical coupler responsive to un-scattered light from the source and to light from the source that has been scattered by a sample, with the detector being responsive to an output of the optical coupler. The detector can be a photon-counting detector. The instrument can further include a modulator for the illuminating light or for a reference beam to differentiate direction of movement. The instrument can also include an optical path for the un-scattered light. The instrument can further include electrophoretic mobility calculation logic responsive to the detector. The instrument can further include zeta potential calculation logic responsive to the detector. The instrument can further include a display operative to present the zeta potential to a user of the instrument. The instrument can further include condition detection logic operative to issue a condition detection signal associated with one of the different sample containers when a predetermined condition is detected for that sample container based on the scattered light. The instrument can further include particle size calculation logic responsive to the detector. The instrument can further include at least one optical fiber between the sample and the detector. The detector can be an image detector. The instrument can further include a bundle of optical fibers between the sample and the detector. The instrument can further include an X-Y stage supporting the camera. The instrument can further include at least one more off-axis scattering detector that is responsive to scattered light after it has interacted with another of the samples.

In another general aspect, the invention features a high-throughput optical suspension characterization instrument that includes a body defining a plurality of sample containment volumes each having a transparent bottom surface. A first electrode is associated with each of the sample containment volumes and positioned to include at least a sample contact surface within the containment volume that it is associated with. A second electrode is associated with each of the sample containment volumes and positioned to include at least a sample contact surface within its containment volume. A top window is associated with each of the sample containment volumes and positioned above at least a portion of the volume that it is associated with.

In preferred embodiments, the instrument can further include a contact pad associated with each of the first electrodes. The second electrodes can be electrically connected together. The container volumes can each include a top void that leaves at least part of a top surface of the sample exposed to ambient conditions.

In a further general aspect, the invention features a high-throughput optical suspension characterization method that includes positioning a selected one of a plurality of liquid samples relative to a source beam, applying an electric field across the selected liquid sample, and detecting light from the source that has been scattered by the selected liquid sample after the step of positioning and during the step of applying. These steps of positioning, applying, and detecting are repeated for further samples.

In preferred embodiments, the method can further include the step of deriving a zeta potential value from the detected light. The method can further include the step of combining unscattered light with the scattered light before the step of detecting for each of the samples. The method can further include the step of providing an optical path for the scattered light through a liquid contact surface to reduce surface effects. The method can further include providing an identification of at least one of the liquid samples based on predetermined conditions detected from the scattered light. The method can be applied to liquid samples that include proteins and wherein characteristics of the proteins are detected in the step of detecting. In another general aspect, the invention features a high-throughput optical suspension characterization instrument that includes means for positioning a selected one of a plurality of liquid samples relative to a source beam, means for applying an electric field across the selected liquid sample, and means for detecting light from the source that has been scattered by the selected liquid sample after positioning with the electric field applied, for a succession of samples.

In a further general aspect, the invention features a high-throughput optical suspension characterization instrument that includes a power supply, a plurality of hydraulically separate sample containers each including a pair of electrodes operatively connected to the power supply, a first light source, and an imaging detector positioned to acquire an image of samples together in the hydraulically separate sample containers as they are illuminated by light from the first light source.

In preferred embodiments the pair of electrodes in each of the containers can be separated from each other by on the order of 1 mm or less. The electrodes can be included in a separate disposable part. The instrument can include a second light source having different spectral characteristics from those of the first light source. The first light source and the second light source can each include a different filter, with the filters being positioned to receive light from a same third light source. The instrument can further include hydrodynamic size value derivation logic responsive to the imaging detector. The instrument can further include electrophoretic mobility value derivation logic responsive to the imaging detector. The hydraulically separate sample containers can each be wells in a 96-well plate. The source can be an ultraviolet source. The imaging detector can be a two-dimensional array detector. The imaging detector can be a linear detector.

In another general aspect, the invention features a high-throughput optical suspension characterization method that includes positioning a plurality of hydraulically separate liquid samples together, illuminating the liquid samples, applying an electric field across each of the liquid samples, and acquiring an image of the plurality of liquid samples during the step of illuminating.

In preferred embodiments, the method can further include the step of acquiring at least one further image of the plurality of liquid samples. The method can further include a step of deriving an electrophoretic mobility value for the samples after the step of acquiring and the step of further acquiring. The method can further include the step of reducing the electric field and acquiring at least one further image of the plurality of liquid samples after initiation of the step of reducing the electric field. The method can further include the step of deriving a hydrodynamic size value for the samples after the step of acquiring at least one further image. The steps of illuminating, applying, and acquiring can be each performed simultaneously for at least about 96 samples. The method can further include a step of positioning at least one reference sample in the source beam and wherein the step of acquiring also acquires information for the reference sample. The method can further include a step of again illuminating the liquid samples but with a different spectral characteristic, and acquiring at least one further image of the plurality of liquid samples during the step of again illuminating. The method can further include the step of deriving particle characteristic values for different types of particles in the samples based on the acquisition steps for the different spectral characteristics. The step of positioning the samples can be performed by a multi-well plate and further including the step of discarding the plate after a single use.

In a further general aspect, the invention features a high-throughput optical suspension characterization method that includes positioning one or more liquid samples in an electroosmotically neutral vessel, illuminating the liquid samples, applying an electric field across each of the liquid samples, acquiring a series of images of the plurality of liquid samples during the step of illuminating, and comparing information from the images to determine one or more properties of one or more types of particles suspended in the liquid sample.

In another general aspect, the invention features a multi-well plate for high-throughput electrophoretic measurements that includes a plurality of electroosmotically neutral walls that define hydraulically separate wells arranged in an array, a first plurality of electrodes, wherein the first plurality of electrodes includes electrodes that are each located in one of the wells, a second plurality of electrodes, wherein the second plurality of electrodes includes electrodes that are each located in one of the wells and separated from the first electrode for that well by a predetermined gap, a first electrical network connected to each of the electrodes in the first plurality and to at least a first electrical supply terminal, and a second electrical network connected to each of the electrodes in the second plurality and to at least a second electrical supply terminal.

In preferred embodiments, the walls defining at least part of the wells can be transparent. The wells and the electrodes can be positioned above a transparent base plate that defines the bottom surfaces of the wells. The plate can define at least 32 or even 96 wells. The electrodes in each of the wells can be positioned to define the predetermined gap in each of the containers to be on the order of 1 mm or less. Tart of the multi-well plate can be disposable. The whole multi-well plate can be disposable. The well spacing of the multi-well plate can be based on the well spacing of a standard commercial multi-well plate.

DETAILED DESCRIPTION OF AN ILLUSTRATIVE EMBODIMENT

This document describes an approach to making an array of measurement cells as an accessory to a conventional, or specially produced, multi-well plate, that can be used for EPM measurements where the wells are measured sequentially without removing the sample and thus avoiding cross-contamination. Note that this is particularly beneficial in the EPM measurement since the process involves passing an electric current through the sample and thus potentially degrading or changing it due to local Joule-heating or other parasitic effects.

Two different optical-based methods for making the measurement are described. The first uses an approach based on the Malvern Zetsizer Nano in which a laser beam is transmitted vertically through the plate and scattered light detected from each well in turn from above. The plate is translated in X-Y to select the wells in turn. A Z motion may be used to bring the optical receiver to the appropriate distance above the selected well and make electrical contact, or simply the latter with the receiver optic being fixed in that case. This approach using the laser Doppler technique is the most sensitive method, but may have a possible drawback in that it can be difficult to thermostat a standard well plate that is accessed from both above and below during the measurement.

Alternate approaches using imaging are also described, and the sample temperature for some of these may be easier to control. But these approaches may also be less sensitive in terms of particle size and magnitude of EPM and change in EPM that can be detected.

Description of Laser Doppler High Throughput System

Figure 1:
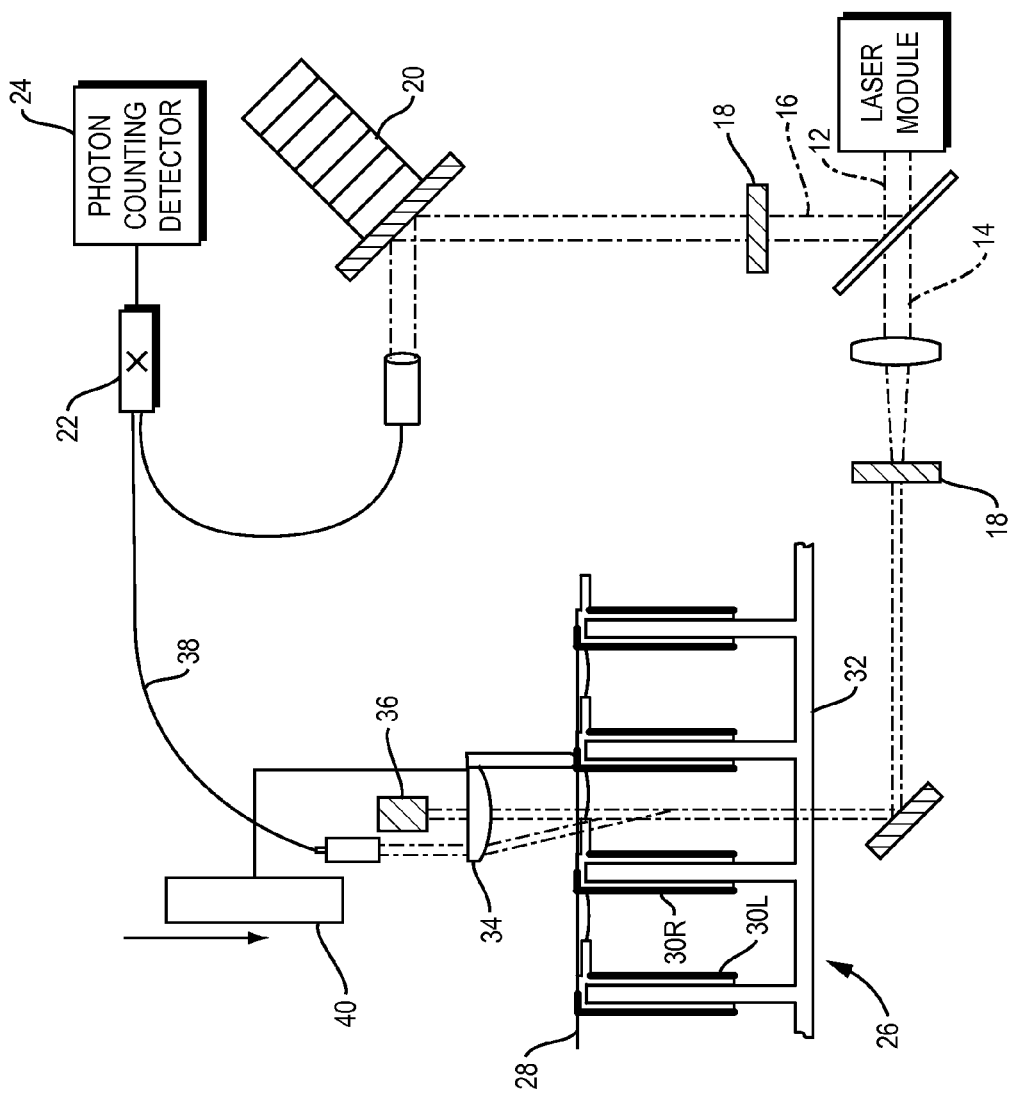
FIG. 1 is a block diagram illustrating a first high-throughput measurement system according to the invention, showing its well plate in cross-section.

Referring to FIG. 1, an optical system derived from the Malvern Zetasizer Nano described in Appendix 1 is used. A laser beam 12 is split into a sample illumination path 14 and a reference beam 16. Each path is provided with an attenuator 18 to select the intensity range so that the reference beam is around 10-100 times more intense than the sample scattering. The reference beam is modulated by a Piezo modulator 20 to provide a frequency offset as is widely done in laser Doppler electrophoresis. This reference beam is then combined with scattered light from the sample probe volume and mixed in a fiber combiner 22 and passed to a photon counting detector 24 that produces electronic pulses for each photon detected. A signal processor then calculates the velocity distribution and hence the EPM and zeta potential.

This process uses a technique known as Phase Analysis Light Scattering which is capable of detecting small frequency shifts and hence low values of EPM, and thus also well adapted to measurements using low electric fields, which is likely to be advantageous in small sample volumes and relatively high conductive samples in or near to physiological conditions likely for some samples of biological or medical interest. This technique as implemented by Malvern in the Zetasizer Nano is described in a paper included as Appendix 2.

The sample is contained in a selected well of a plate 26 with a special molded plastic cover plate 28 incorporating pairs of electrodes 30L, 30R to match with each well in a 96 or perhaps 384 well plate. The electrodes are made of metal or other conductive film stuck to downward projections so that a gap of about 2 mm is left. Through this gap the laser beam passes through the transparent base 32 of the plate and is focused by a receiver lens 34 to a beam dump 36 that could include a light transmission monitor detector. The lens also collects scattered light and a fiber 38 is positioned parallel to the axis so that light from a particular range of scattering angles (in the preferred implementation around 12 degrees) is collected by the single-mode detection fiber and then passed to the combiner 22 and then to the photon detector 24.

The well plate can be positioned by an X-Y stepper motor driven stage so that each or any well can be measured in turn. In one preferred scheme the electrodes pairs are selected by moving the optical head away from the plate during the x-y translation process then moving it downward before the measurement starts so that a contact point presses onto one of the two electrodes that has a fold onto the top surface of the molding. The other electrodes (the 'Left' or 'L' set) are interconnected so that the circuit to the selected well is completed by the single contact. This enables the other side of the well to be covered by a window molding and so ensure that the scattered light is not passed through the meniscus and diverted in an unpredictable way.

The Z motion may be applied only to the electrical connection leaving the receiver lens in a fixed relationship to the laser beam optics below the plate. It may be possible to avoid fitting this Z drive 40 if the contacts were made by a roller that scanned the plate using only spring loading to make contact but this could be a less reliable proportion.

In another implementation both electrodes are probed from above the connection to the Left set being by some tortuous path still allowing the window to be positioned to allow scattered light through.

Note that it can be undesirable to power all the wells simultaneously as the measurement can be intrusive and samples would be degraded before they were selected for measurement.

Since the electrodes are close to the walls of the well and in particular the bottom and top windows electro-osmosis is likely to be present. This is a collective motion of the suspending liquid itself due to the application of the electric field and the ionic nature of the liquid. This may be countered while still permitting high quality EPM measurements using the method described as Mixed Mode Measurement (M3) in the earlier patent referenced above.

Figure 2:
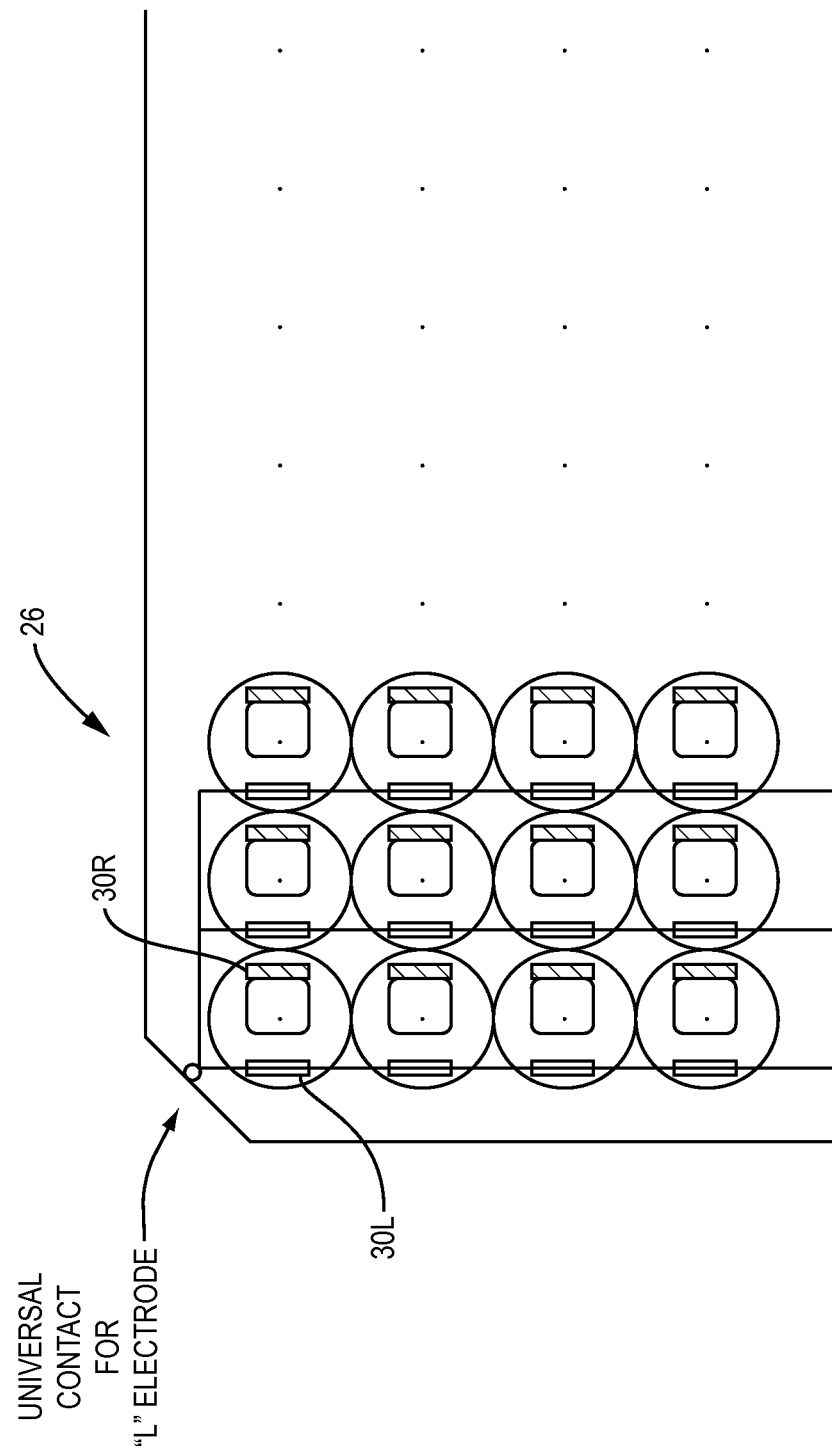
FIG. 2 is a partial plan view of the well plate shown in FIG. 1.

The optical arrangement is shown in a sketch from the side and the plate molding from above in the accompanying FIGS. 1 and 2.

Thermal control has not been detailed but should apply to the atmosphere around the plate or perhaps special fluid networks incorporated in the plate holder or special electrode molding.

First Imaging Method Description

This is based on a similar design of plate electrode molding as the laser Doppler approach just described. The single mode fiber receiver is replaced by large size (1-2 mm) core fibers. One is used to transmit white or monochrome light to illuminate the sample well and illuminate the sample. The other is connected to a digital camera that collects an image at up to 100 times a second. Image analysis is used to track individual particles and calculate the electrophoretic mobility. This may be limited to particles >1 micron (probably ~5 microns) and may be less sensitive by several orders of magnitude. However it should be able to detect a large change in EPM when a binding effect leads to neutralization or charge reversal. It is a simpler and cheaper approach and would allow the plate to be mounted on a conventional thermal control system. Another approach is to mount the camera directly on an x-y stage without the fiber optic bundle.

Second Imaging Method Description

Figure 4:
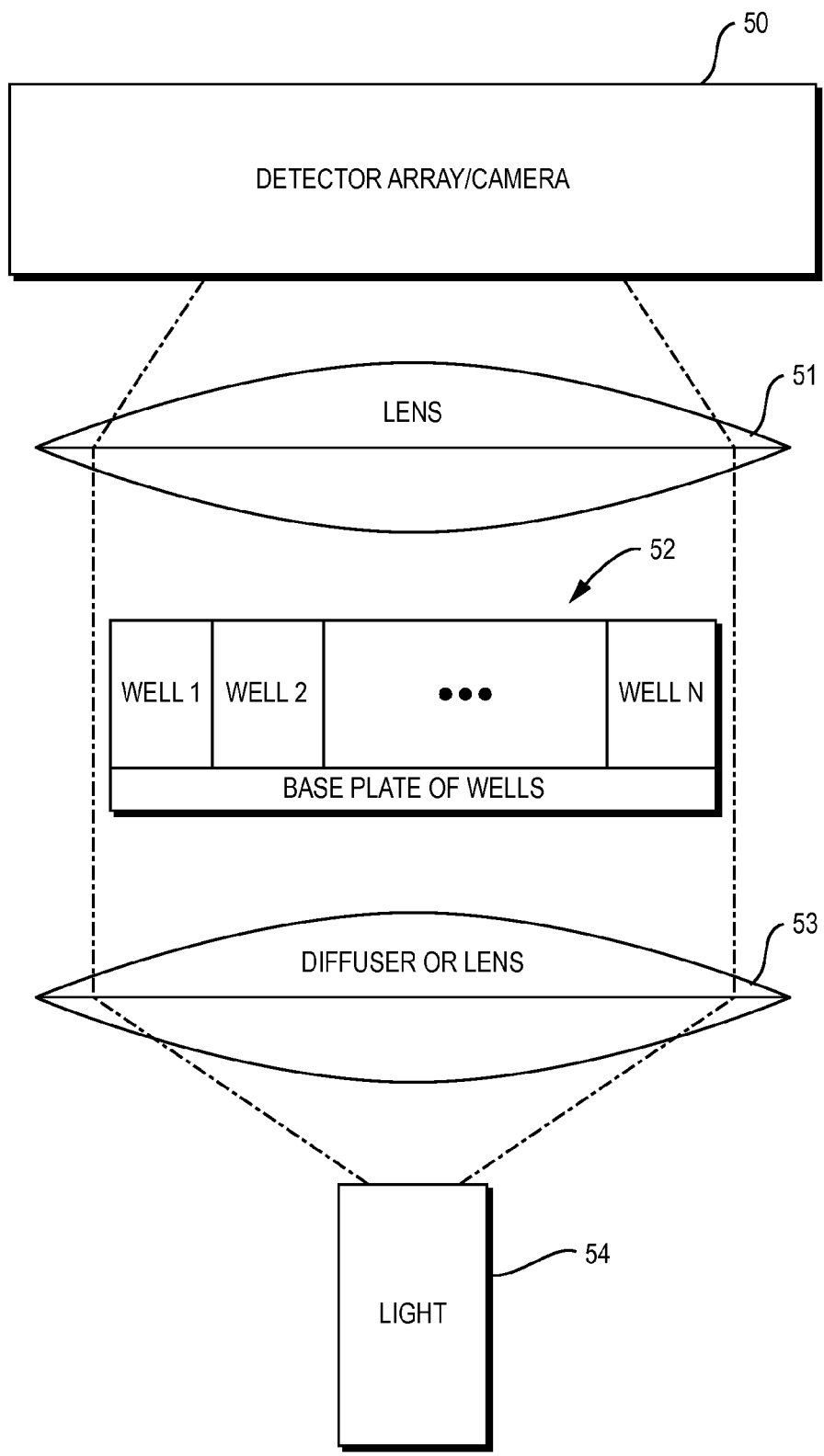
FIG. 4 is a block diagram illustrating a second high-throughput measurement system according to the invention, showing its well plate in cross-section.

Referring to FIG. 4, a cell or array of cells 52 containing a dispersion of particles or macro molecules can be illuminated through the base by a substantially uniform visible or ultraviolet light source 54. The most appropriate wavelength will be where the sample particles or molecules possess sufficient absorbance to be detected at low concentrations (~1 mg/ml) over the path length through the cell. This is likely to be a few millimeters. This is the same situation as occurs in standard spectrophotometers so the applications are not likely to be limited by this requirement. A lens or diffuser 53 may be incorporated to produce a suitable light propagation through the sample plate.

Each cell contains a pair of electrodes of spacing probably in the range 0.5 to 1 mm. In the case of a multi-well plate these can be interdigitated and connected in parallel. Since the electrodes are close together quite high electric fields (20-30 v/cm) can be produced by a low voltage (<5 volts).

The transmitted light is collected by a camera or detector array 50 that has sufficient resolution to select the region between the electrodes where light will be partially transmitted depending on the concentration and specific absorbance of the sample. A lens 51 may be included to form the image of the plate area on the detector.

The measurement process begins with the application of a field (A DC voltage). If the particles are charged they will migrate toward the opposite polarity electrode. The transmitted light will therefore increase as the suspension is depleted, and an estimate of the electrophoretic mobility can be made from the time taken for the change in transmission over a length scale set by the electrode spacing. If the imaging is sufficiently sensitive the direction may be seen by the existence of a gradient across the image.

Figure 5:
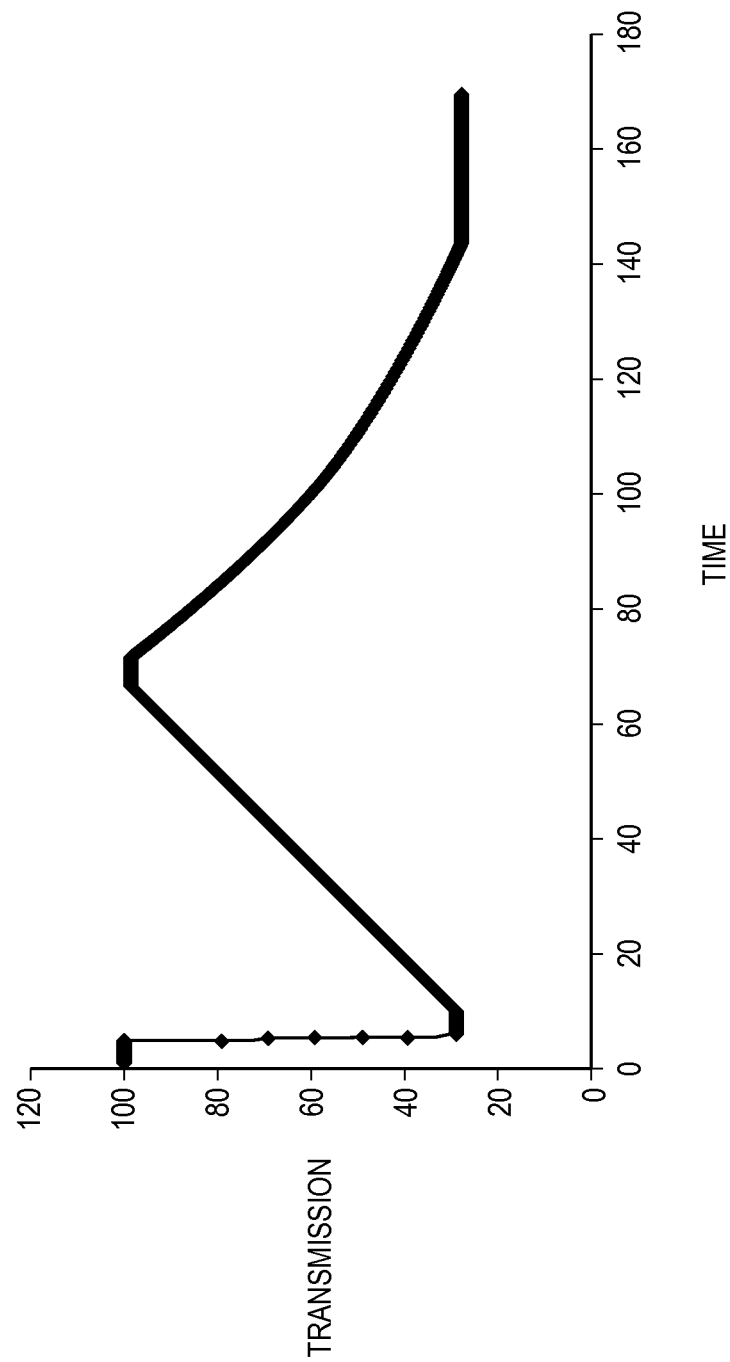
FIG. 5 is an illustrative plot of transmitted intensity against time for the system of FIG. 5.

The field is then removed and the intensity monitored. The particles will diffuse under Brownian motion and therefore the transmitted intensity will increase again, and the time taken to reach a steady state can be used to estimate the hydrodynamic size by applying the Stokes-Einstein relationship to the measured diffusion coefficient. A sketch of the timing of this is shown as FIG. 5.

This measurement may be made in all wells simultaneously as no complex signal processing is required. The location of the pixels that are matched to individual wells can be established by locating the variation in transmission in different regions across the plate at the start of the measurement. The centre of well would generally be near to minimum in transmission (away from structure imposed by the plate itself) for a dispersion of molecules or particles, a maximum for a 'fluid only' reference sample. Some wells could contain clear suspension fluid only to establish a baseline.

Mobility Determination

Effective spacing 1 mm. Applied voltage 3=30 v/cm. Zeta potential 40 mV~mobility 3 microns/second per v/cm=>time to clear cell~11 seconds. Hence measurement times of 10-100 seconds should suffice to classify Zeta potential into decades 0-10, 10-20, 20-30, >30, which should suffice for screening.

The choice of actual voltage used will depend on application, actual electrode spacing which may be different from 1 mm, and the conductance of the sample. Since in the preferred embodiment all the cells are connected in parallel only an average figure for conductivity can be measured.

Size Determination

Time to diffuse 1 mm. For a 4 nm radius particle (a BSA monomer MW 66500 Da) the diffusion speed in water at 25 degrees centigrade is 7.8 microns/second so the well should refill in 128 seconds. Given that perhaps 96-384 samples could be measured simultaneously this seems an acceptable time.

The ratio of mobility to diffusion coefficient can be established without requiring the actual electrode spacing so this directly observable quantity may be useful as a screening value.

Concentration Determination

If the path length through the cell is known and the absorbance coefficient has been measured the sample concentration can be established and also the relative concentration of the charged population to uncharged assuming the sample was not homogeneous in that respect.

A number of standard samples may be placed in different wells across the plate as a control and to provide absolute calibration of the concentration.

For hetereogeneous samples the use of two or more than one wavelengths may give additional resolution. The different wavelengths can be provided in a variety of ways, such as with separate sources, with a single source and a variable filter or filter wheel, or with a tunable source.

Plate Construction

The base will be a transparent (at the wavelengths to be used, say 280 nm) plate around 1 mm thick. Electrodes will be laid down as parallel arrays of wires perhaps using lithographic techniques. An interdigitated arrangement can be used, where alternate rows are cross connected at opposite ends and a single pair of connections made to the electrophoresis power supply. A grid of cells is then deposited on the plate to hold individual sample specimens. Since electro-osmosis must be avoided or reduced, the plate in contact with sample will be coated with a neutral polymer such as PVP (poly vinyl pyrrolidine) or Methyl Cellulose, or perhaps a silane based compound. The plates can be supplied as consumable items.

Although the electrode spacing of 1 mm has been used as the basis for discussion, a closer spacing of say 100 microns may be practical, in which case measurement times would likely be reduced. It may not be possible to measure the sign of the mobility (direction of movement) in that case, and precision may be reduced. However this is a property of the particular form of plate, other parts of the apparatus being relatively unaffected, so a range of plates trading or performance against throughput can be envisaged.

The imaging detector need not necessarily image all wells simultaneously but can instead scan them sequentially sufficiently rapidly that the time dependant information needed is obtained by re-imaging a well or group of wells within a sufficiently short period. For example, a linear array of detectors can scan across the plate either mechanically or via optical adjustment, in a manner similar to that employed by a flat-bed scanner (e.g., using a scanning mirror). A single detector could also be scanned in the X and Y directions. These approaches can use a smaller number of sufficiently sensitive detectors, which might be too expensive, bulky, or otherwise inconvenient to include as a complete X-Y array.

In the embodiment described, control and measurement functions can be performed by a computer workstation running a standard operating system, such as Microsoft Windows® or Linux®, and special-purpose software. The workstation can allow the user to perform individual measurements, and it can also use sequencing functionality to fully automate all of the operations electrical and mechanical operations necessary to process a tray or a series of trays, and provide the user with a list of the containers that meet user-specified conditions. It is also possible to create an implementation that is based on specialized custom hardware, or a combination of the two approaches. The sample tray and electrodes can be reusable or disposable and can be made of a variety of materials, such as polycarbonate with gold on beryllium-copper.

Multiple imaging or non-imaging probes could also be provided, to increase throughput. Four probes, for example, could simultaneously collect images from four adjacent wells. These wells would be simultaneously powered by the Power Supply Unit (PSU).

Numerous modifications which are contemplated as falling within the scope of the present invention should also now be apparent to those skilled in the art. For example, the shape of the sample containers and their windows can be varied considerably while still allowing appropriate measurements to take place. A reflective configuration that employs an imaging array can also be constructed, using a beam splitter. And different types of approaches can be used to select a sample container, such as moving the laser and detector, moving the plate, or moving one or more other optical elements such as mirrors. It is therefore intended that the scope of the present invention be limited only by the scope of the claims appended hereto. In addition, the order of presentation of the claims should not be construed to limit the scope of any particular term in the claims.

The Malvern Instruments Zetasizer Nano (Appendix 1)

Malvern Instruments Zetasizer Nano series is a family of instruments using light scattering to characterize small particles or large molecules in dispersions or solutions. Depending on the model of instrument the size and molecular weight and/or zeta potential, the effect of electrical charge on the particle surface, can be determined.

The general mode of operation is similar for each measurement. A sample is prepared by dispersing the material is a suitable solvent or dispersing liquid at a concentration that may be up to 40% solids (by volume) but is usually much lower. For the molecular weight measurement the concentration should be accurately known, for molecular or particle size the concentration can be approximately determined as part of the measurement process and need not be known in advance. For the zeta potential measurement the concentration is less important. In all cases the concentration should be large enough that the excess scattering above the solvent is sufficient to give a measureable signal. This minimum concentration is dependent on size and refractive index.

The sample is placed in a transparent cuvette (also called a cell) which is inserted into the instrument through a manually operated lid. There is a range of cell types suitable for different applications, some types cater for several. The light source is a nominal 4 mW HeNe laser (there is a higher power model as well) which illuminates the a small region of the sample through an optical train incorporating a selectable attenuator that is usually adjusted automatically to set the signal level in an optimum range for the photon counting detector that collects scattered light and quantifies it as a number of photon detections in a given time. The detector is a commercially available photon counting model manufactured by Perkin Elmer.

The sample cell is held in a temperature regulated enclosure that may be controlled between 0 and 90 degrees C. on standard instruments. An extended range up to 120 is also available.

The output from the detector is fed to a signal processing card manufactured by Malvern that can perform a number of functions. For the molecular weight measurements the count rate from a number of samples of the same material at known different concentrations are compared to the scattering from a toluene reference sample. This type of measurement is also known as static light scattering. Particle or molecular size measurement is usually determined from a single concentration sample by dynamic light scattering; in this operation fluctuations in the scattered light intensity are analyzed and allow the movement of particles by Brownian motion to be determined. This can be related to hydrodynamic size by a simple equation. For more concentrated samples the determination can be more complex as sample interactions (particles colliding) and multiple scattering (photons scattering several times before detection) can become an issue.

The zeta potential determination is performed in special cells fitted with electrodes. An electric field is applied to the sample and that causes any charged particle in the sample to migrate toward the electrode of opposite polarity. This movement causes a Doppler shift in the scattered light that can be measured as a frequency shift by mixing the scattered light with a modulated reference beam. This frequency shift is seen as regular fluctuations in the scattered intensity measured by the signal processor.

Figure 3:
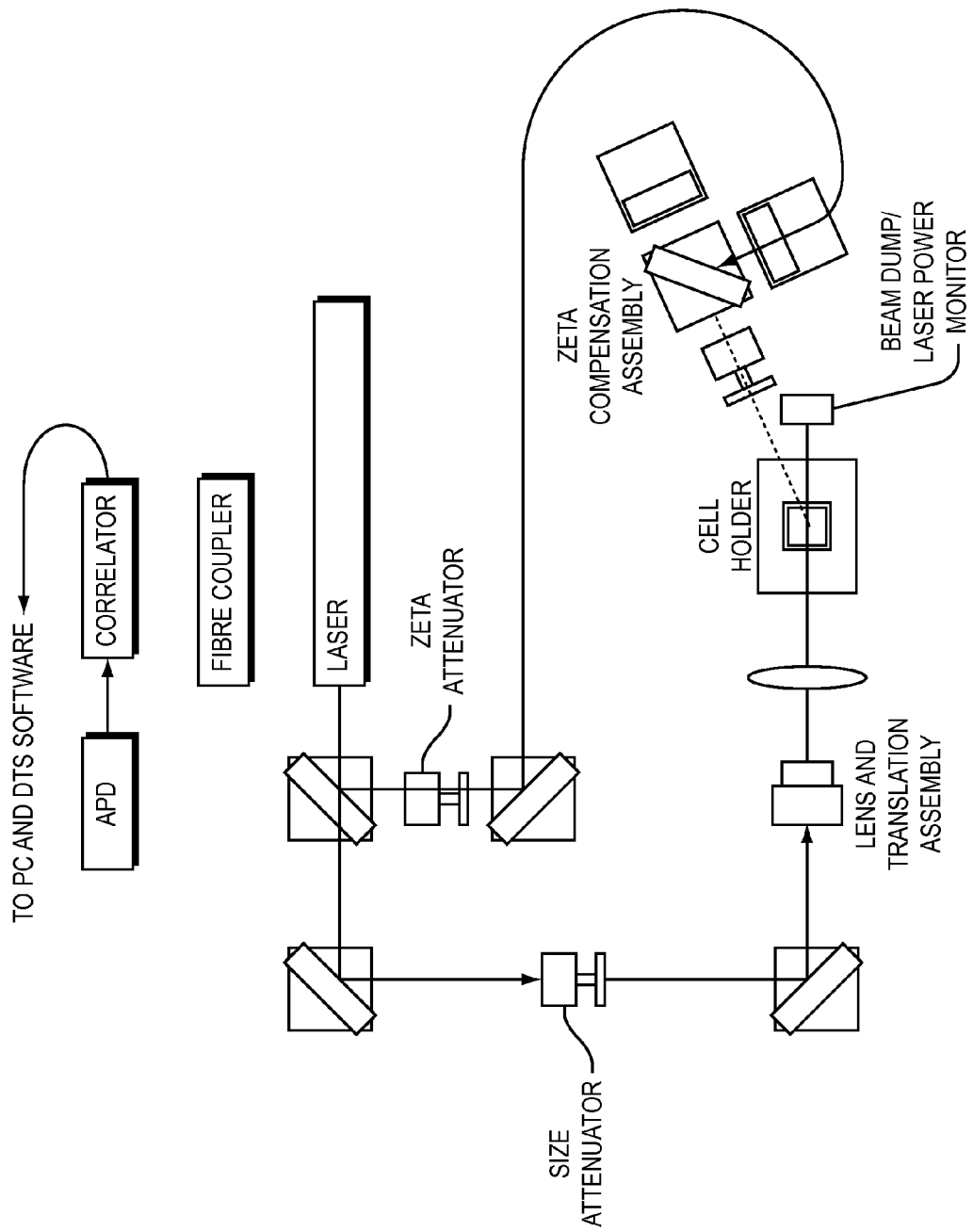
FIG. 3 is an optical diagram for a scattering instrument suitable for use in the system of FIG. 1.

The optics of the Zetasizer Nano are shown in FIG. 3.

Phase Analysis Light Scattering as Implemented in the Malvern Zetasizer (Appendix 2)

Phase Analysis Light Scattering (PALS) is useful for measuring small frequency shifts in period signals. Such a signal arises in a laser Doppler velocimeter when scattered light from moving particles is mixed with a fraction of the illuminating laser and a beat frequency is observed at the detector. The beat frequency arises because of the frequency shift caused by the motion of the particles.

During electrophoresis the particles are in motion because they possess a charge which gives rise to a small zeta potential and are immersed in an electric field applied to the suspending fluid. The details of this arrangement and the origins of zeta potential are well known and are beyond the scope of this document.

The illuminating (laser) light has a high frequency—far too high for the oscillations to be detected directly—around $10^{14}$ Hz. However the frequency shift is much lower, and depends not only on the wavelength and velocity but also on the angle through which the light is scattered.

The frequency shift is in fact:

$$\Delta f = 2v \sin\left(\frac{\theta}{2}\right) / \lambda \tag{1}$$

where v is velocity, $\lambda$ is wavelength, and $\theta$ is the scattering angle. For a velocity of 1 m/s and a small scattering angle this shift will therefore be around 1 MHz since the wavelength will be around $5 \times 10^{-7}$ m.

The beat frequency we observe is simply this shift frequency.

In microelectrophoresis the velocities that are observed are much lower, typically around 10's of microns/second, and hence the frequency shifts are ~10 Hz. In the Zetasizer our 'standard' DTS50 particles in a field of 150V across the roughly 50 mm length of the folded capillary cell have a frequency shift of 50 Hz.

In the Zetasizer, and other some other velocimetry arrangements, it is important that the sign as well as magnitude of the shift can be measured. In order to do this the light taken directly from the laser beam is modulated so that it is itself shifted in frequency away from the fundamental. If we express the frequencies used as circular frequencies so that $\omega = 2\pi f$ (i.e., 1 cycle is $2\pi$), then the optical mixing of the scattered and direct but modulated light is expressed as the product of two sine waves (phase factors omitted for simplicity).

The intensity observed at the detector is $$I(t) = S_0 \sin((\omega_0 + \Delta\omega)t) + A_0 \sin((\omega_0 + \omega_M)t))^2 \quad (2)$$

Where $\Delta\omega$ is $2\pi\Delta f$, the circular Doppler frequency shift, and $\omega_M$ is the modulation frequency applied. A is the amplitude of the direct or 'reference' beam, S that of the scattered light from the moving particles.

This result will not be derived in detail but it turns out that only the low frequency terms are detected and the relevant one that we observe is $$I(t) = A_0 S_0 \sin((\omega_M + \Delta\omega)t) \quad (3)$$

Now the sign, as well as magnitude, of the frequency shift can be observed as long as $\omega_M > \Delta\omega$.

In the Zetasizer the modulator frequency is typically around 300 Hz, so frequency shifts up that value can be accurately measured. Zeta potentials larger than around 120 mV do not occur, so even if 150 V is applied frequency shifts will be less than around 120 Hz, and of course the applied voltage can always be reduced. Note that stationary particles scatter 'at the modulator frequency' and we arrange that negative zeta potentials give rise to $\Delta\omega < 0$, and $\Delta\omega > 0$.

So far we have discussed a single frequency shift arising from a population of particles in a fixed electric field all moving with the same velocity. In fact a spectrum of velocities is observed, since even a population of similar particles will undergo random Brownian motion as well as directed motion in the electric field.

Of course if populations with different zeta potentials are present several frequencies will be present. This is dealt with by performing spectral analysis—usually a Fourier transform to decompose the different frequencies present into a distribution usually plotted as a graph of signal against frequency. Hence populations can be distinguished by frequency and signal strength, which is related to the number of particles with that zeta potential.

Two narrow 'spikes' frequencies can be distinguished in a spectrum if sufficient samples of the waveform are taken, but for practical reasons in an instrument such as the Zetasizer the number of samples tends to be limited to a few thousand at a rate of up to 1 ms per sample. This implies that we can distinguish two frequencies spaced by around 1 Hz. For real samples, we could hardly distinguish two 'peaks' at such spacings since Brownian motion and other sources of noise tend to 'blur' the spectra.

However much smaller frequency shifts can occur when either zeta potential is low, or the velocity that arises when the field is applied is low for other reasons. The suspending liquid can be much more viscous than water, or have low dielectric constant for example.

$$\text{mobility} = \text{velocity/electric field} \sim \text{zeta potential} * (\text{dielectric constant/viscosity})$$

In these cases we have the task of distinguishing a small shift away from the modulator frequency, (<<1 Hz), and the Fourier transform, at least in the presence of Brownian motion and other sources of noise, and over the finite data length we can use cannot do this.

Phase analysis enables the measurement of a small change in the modulator frequency. If we multiply our signal by sine and cosine waves generated mathematically at the frequency of the modulator and filter out the high frequency ($2\omega$) terms, the result is two derived functions referred to as I and Q, the In phase and Quadrature components.

The Arctangent of the ratio of these functions is the phase difference between our mathematically generated sine wave and the actual signal. The absolute value of this is arbitrary, but its rate of change is simply the difference between the frequency of the signal and our test waveforms.

Rate of change of phase is by definition frequency, since phase=frequency×time.

By this method it is possible to measure a change with respect to the modulator frequency of as little as 0.001 Hz.

In the Zetasizer an AC field is applied to avoid polarizing the cell, and to avoid electroosmosis. In the capillary cell we reverse the field at around 50 Hz (FFR or fast field reversal), to measure only electrophoresis, and hence the mean zeta potential. The field is also applied at around 1 Hz (SFR—slow field reversal to measure the spectrum of velocities and hence zeta potential, though this measurement also adds the velocity caused by the charge on the cell wall through the phenomena of electro-osmosis.

We can therefore subtract a velocity that makes the spectrum agree with that predicted by the FFR stage, that velocity is the electro-osmotic velocity and enable us to calculate the zeta potential of the cell wall.

For very low mobilities the spectrum will simply have a peak near the modulator frequency: no other spectral due to zeta potential differences will be distinguishable, but the PALS technique enables us to locate that peak at its small shift from the modulator value very accurately.

Features of the dependent claims may be combined with those of the independent claims in any number and combination to provide preferred embodiments of the invention.

The invention claimed is:

1. A high-throughput optical suspension characterization instrument, comprising:
   a plurality of hydraulically separate and at least partially transparent sample containers,
   a light source,
   a first electrode associated with each of the sample containers and positioned to include at least a sample contact surface within the container that it is associated with,
   a second electrode associated with each of the sample containers and positioned to include at least a sample contact surface within its container,
   means for applying an electric field across selected pairs of the first and second electrodes,
   a selection mechanism operative to selectively direct light from the light source through different ones of the sample containers along an optical axis,
   an off-axis scattering detector responsive to scattered light from the light source after it has interacted with a sample,
   zeta potential calculation logic responsive to the detector and operative to calculate a zeta potential from a Doppler shift detected by the detector, and
   a display responsive to the zeta potential calculation logic and operative to present the zeta potential to a user of the instrument.

2. The apparatus of claim 1 wherein the selection mechanism is operative to move the sample containers together relative to the light source and the detector.

3. The apparatus of claim 2 wherein the selection mechanism includes a motorized X-Y stage.

4. The apparatus of claim 2 wherein the selection mechanism includes a motorized X-Y-Z stage.

5. The apparatus of claim 1 wherein the sample containers are part of a unitary sample container array.

6. The apparatus of claim 5 wherein the sample containers are part of a 96-well plate.

7. The apparatus of claim 1 wherein the light source is a laser.

8. The apparatus of claim 1 further including a top window associated with each of the sample containers that includes at least a portion located in an off-axis scattering path between a light source position and the scattering detector.

9. The apparatus of claim 8 wherein each window is a partial window and is integral to one of the sample containers.

10. The apparatus of claim 1 wherein the electrodes are integral to the containers.

11. The apparatus of claim 1 further including sequencing logic operative to cause the selection mechanism to successively select and perform a measurement for each of a plurality of the different sample containers.

12. The apparatus of claim 1 further including an optical coupler responsive to un-scattered light from the source and to light from the source that has been scattered by a sample, and wherein the detector is responsive to an output of the optical coupler.

13. The apparatus of claim 12 where the detector is a photon-counting detector.

14. The apparatus of claim 12 further including a modulator in and optical path for the un-scattered light.

15. The apparatus of claim 1 further including electrophoretic mobility calculation logic responsive to the detector.

16. The apparatus of claim 1 further including at least one optical fiber between the sample and the detector.

17. The apparatus of claim 1 further including a contact pad associated with each of the first electrodes.

18. The apparatus of claim 1 wherein the second electrodes are electrically connected together.

19. The apparatus of claim 1 wherein the container volumes each include a top void that leaves at least part of a top surface of the sample exposed to ambient conditions.

20. A high-throughput optical suspension characterization instrument, comprising:
a plurality of hydraulically separate and at least partially transparent sample containers,
a light source,
a first electrode associated with each of the sample containers and positioned to include at least a sample contact surface within the container that it is associated with,
a second electrode associated with each of the sample containers and positioned to include at least a sample contact surface within its container, wherein the electrodes are part of a removable electrode assembly,
a selection mechanism operative to selectively direct light from the light source through different ones of the sample containers along an optical axis, and
an off-axis scattering detector responsive to scattered light from the light source after it has interacted with a sample.

21. A high-throughput optical suspension characterization instrument, comprising:
a plurality of hydraulically separate and at least partially transparent sample containers,
a light source,
a first electrode associated with each of the sample containers and positioned to include at least a sample contact surface within the container that it is associated with,
a second electrode associated with each of the sample containers and positioned to include at least a sample contact surface within its container,
a selection mechanism operative to selectively direct light from the light source through different ones of the sample containers along an optical axis,
an off-axis scattering detector responsive to scattered light from the light source after it has interacted with a sample, and
an electrical probe associated with a receiving lens and wherein the electrical probe is operative to selectively make an electrical connection to one of the electrodes for a selected one of the sample containers.

22. The apparatus of claim 21 wherein the selection mechanism includes a motorized mechanism operative to position the probe vertically.

23. The apparatus of claim 21 further including condition detection logic operative to issue a condition detection signal associated with one of the different sample containers when a predetermined condition is detected for that sample container based on the scattered light.

24. The apparatus of claim 21 further including particle size calculation logic responsive to the detector.

25. A high-throughput optical suspension characterization instrument, comprising:
a plurality of hydraulically separate and at least partially transparent sample containers,
a light source,
a first electrode associated with each of the sample containers and positioned to include at least a sample contact surface within the container that it is associated with,
a second electrode associated with each of the sample containers and positioned to include at least a sample contact surface within its container,
a selection mechanism operative to selectively direct light from the light source through different ones of the sample containers along an optical axis, and
an off-axis scattering detector responsive to scattered light from the light source after it has interacted with a sample, wherein the detector is an image detector.

26. The apparatus of claim 25 further including a bundle of optical fibers between the sample and the detector.

27. The apparatus of claim 25 further including an X-Y stage supporting the camera.

28. A high-throughput optical suspension characterization instrument, comprising:
a plurality of hydraulically separate and at least partially transparent sample containers,
a light source,
a first electrode associated with each of the sample containers and positioned to include at least a sample contact surface within the container that it is associated with,
a second electrode associated with each of the sample containers and positioned to include at least a sample contact surface within its container,
a selection mechanism operative to selectively direct light from the light source through different ones of the sample containers along an optical axis,
an off-axis scattering detector responsive to scattered light from the light source after it has interacted with a sample, and
at least one more off-axis scattering detector that is responsive to scattered light after it has interacted with another of the samples.

29. A high-throughput optical suspension characterization method, comprising:
positioning a selected one of a plurality of liquid samples relative to a source beam, applying an electric field across the selected liquid sample,
detecting light from the source that has been scattered by the selected liquid sample after the step of positioning and during the step of applying,
repeating steps of positioning, applying, and detecting for a plurality of further samples,
calculating zeta potentials for the samples from Doppler shifts detected in the steps of detecting and repeating, and
displaying the calculated zeta potentials.

30. The method of claim 29 further including the step of combining unscattered light with the scattered light before the step of detecting for each of the samples.

31. The method of claim 29 further including the step of providing an optical path for the scattered light through a liquid contact surface to reduce surface effects.

32. The method of claim 29 providing an identification of at least one of the liquid samples based on predetermined conditions detected from the scattered light.

33. The method of claim 29 wherein the method is applied to liquid samples that include proteins and wherein characteristics of the proteins are detected in the step of detecting.

34. A high-throughput optical suspension characterization instrument, comprising:
    means for positioning a selected one of a plurality of liquid samples relative to a source beam,
    means for applying an electric field across the selected liquid sample,
    means for detecting light from the source that has been scattered by the selected liquid sample after positioning with the electric field applied, for a succession of samples, and
    means for calculating zeta potentials for the samples from Doppler shifts detected by the means for detecting, and
    means for displaying the calculated zeta potentials.

* * * * *